United States Patent [19]

Koch et al.

[11] Patent Number: 4,467,098

[45] Date of Patent: Aug. 21, 1984

[54] PROCESS FOR THE MANUFACTURE OF SUBSTITUTED 3-HYDROXY-1,2,4-TRIAZOLES

[75] Inventors: Manfred Koch, Eppstein; Gerhard Stähler, Frankfurt am Main, both of Fed. Rep. of Germany

[73] Assignee: Hoechst Aktiengesellschaft, Frankfurt am Main, Fed. Rep. of Germany

[21] Appl. No.: 366,320

[22] Filed: Apr. 7, 1982

[30] Foreign Application Priority Data

Apr. 9, 1981 [DE] Fed. Rep. of Germany ....... 3114314
Apr. 9, 1981 [DE] Fed. Rep. of Germany ....... 3114316

[51] Int. Cl.$^3$ .......................................... C07D 249/12
[52] U.S. Cl. ..................................... 548/263; 548/265

[58] Field of Search ................................. 548/263, 265

[56] References Cited

U.S. PATENT DOCUMENTS 3,862,124 1/1975 Dawes et al. ................. 548/263
3,862,957 1/1975 Dawes et al. ................. 548/263

OTHER PUBLICATIONS

Widman et al., Ber. Deut. Chem. Gesel., vol. 26, pp. 2612–2617, (1893).

*Primary Examiner*—Alton D. Rollins
*Attorney, Agent, or Firm*—Curtis, Morris & Safford

[57] ABSTRACT

Manufacture of 3-hydroxy-1,2,4-triazoles by cyclization of corresponding semicarbazides by formic acid in the presence of an inorganic acid or halide thereof.

13 Claims, No Drawings

PROCESS FOR THE MANUFACTURE OF SUBSTITUTED 3-HYDROXY-1,2,4-TRIAZOLES

3-Hydroxytriazoles of the formula I are known intermediates for the manufacture of insecticides (cf. German Pat. Nos. 910,652; 1,299,924; 1,670,876; German Offenlegungsschriften Nos. 2,251,074; 2,251,075; 2,251,096; 2,352,141; 2,352,142).

It is known to prepare 1-phenyl-3-hydroxy-1,2,4triazole by heating 1-phenyl semicarbazide with formic acid (Chem. Ber. 26, 2613 (1893)). However, this process, although using a great excess of formic acid and requiring long reaction times, gives a yield of less than 50% of the theory and is therefore unsatisfactory.

It is further known to prepare compounds of the formula I by reacting corresponding semicarbazides with orthoformic acid esters (cf. German Offenlegungsschrift No. 1,251,074).

It has now been found that the yield can be greatly improved and the reaction time reduced by carrying out the reaction with formic acid with the addition of inorganic or strong organic acids or their halides or anhydrides.

The present invention therefore relates to a process for the manufacture of substituted 3-hydroxy-1,2,4-triazoles by cyclization of correspondingly substituted semicarbazides with formic acid, which comprises carrying out the reaction in the presence of an inorganic or strong organic acid, or their halides or anhydrides.

The process according to the invention yields 3-hydroxytriazoles of the formula I

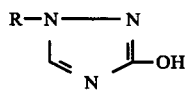  I which are substituted in position 1. The type of the substituent R is of no importance for a successful reaction, provided that R is inert under the reaction conditions. R is preferably a substituted or unsubstituted aliphatic, cycloaliphatic or aromatic radical. Examples hereof are: $(C_1-C_8)$alkyl, $(C_1-C_4)$alkoxy-$(C_1-C_4)$alkyl, cyano-$(C_1-C_4)$alkyl, halogeno-$(C_1-C_4)$alkyl, $(C_3-C_7)$-cycloalkyl; $(C_6-C_{10})$-aryl optionally substituted by one or two substituents selected from the group consisting of $(C_1-C_4)$alkyl, $(C_1-C_4)$alkoxy, $(C_1-C_4)$alkylthio, halogen, trifluoromethyl, cyano, nitro and $(C_1-C_4)$alkoxycarbonyl and benzyl optionally substituted by one or two substituents selected from the group consisting of $(C_1-C_4)$-alkyl, $(C_1-C_4)$alkoxy, halogen and nitro.

At least the stoichiometric quantity of 1 mol, preferably of 2 to 3 mols, of formic acid, per mol of semicarbazide is required to obtain high yields. Greater quantities are not harmful, but offer no advantages either. Formic acid may be used in undiluted form, preferably, however, an inert solvent or diluent is added. Examples of suitable solvents or diluents are water, hydrocarbons such as toluene or xylene, chlorohydrocarbons such as chlorobenzene or carbon tetrachloride, nitriles such as propionitrile or amides such as dimethyl formamide. Water is preferred. The quantity of the inert solvent or diluent is in the range from zero to 500 ml per mol of semicarbazide. Formic acid may be diluted to ten times its original volume, higher dilution degrees are not recommended. If water is used as solvent or diluent, the water content should be preferably from 15 to 85%, in particular from 50 to 80%.

As acids there may be used any known strong acids, in particular sulfuric acid, hydrochloric acid, gaseous hydrogen chloride, chlorosulfonic acid, phosphoric acid and p-toluenesulfonic acid. Suitable acid halides are preferably inorganic acid chlorides and bromides which decompose with the water present to give acids. Examples hereof are: thionyl chloride, sulfuryl chloride, phosphorus trichloride or tribromide, phosphorus pentachloride and phosphorus oxychloride. Phosphorus pentoxide is a suitable acid anhydride. The quantity of these acid additives is preferably in the range from 0.05 to 0.5 mol, in particular from 0.1 to 0.3 mol, per mol of semicarbazide.

The reaction temperature should be above 80° C. and may be up to 150° C. if the operation is carried out under pressure. Under normal pressure the reaction temperature is preferably 90° to 100° C. The reaction time depends on the quantity of formic acid and inorganic acid used and is generally in the range of one to 24 hours. The reaction products may be isolated in simple manner by suction-filtering the precipitated triazole. If the content of aqueous formic acid is higher, dilution of the reaction mixture with water prior to work-up is recommended.

The mother liquor obtained upon separation of the reaction product can be used for further batches, it being only necessary to replace the quantities of semicarbazide, formic acid and of inorganic acid consumed. If desired, the formic acid may be separated from the mother liquor by adding an alcohol and distilling off the ester formed. Formic acid may be further recovered by azeotropic distillation, for example of the azeotropic mixture formic acid/water or formic acid/xylene/water. Formic acid may finally be recovered by extraction from the aqueous solution for example with N,N-dibutyl formamide and subsequent distillation.

In this manner the starting materials are consumed almost completely and substantially without remaining wastes, in contrast to the process hitherto known.

A further advantage of the process of the invention is that it may be performed together with the process for the manufacture of the semicarbazide used as starting compound in a single vessel. Semicarbazides of the formula II

are obtained by reacting the corresponding hydrazine hydrochlorides or acetates with potassium cyanate in water (cf. Ann. 190, 113; Ber. 25, 2613) or by reacting the free hydrazines or hydrochlorides thereof with urea (cf. Gazz. chim. Ital. 16, 202; Ber. 20, 2359). Hitherto it was necessary to isolate and purify semicarbazides obtained in the first step for further reaction. This has considerable disadvantages, as hydrazines do not react quantitatively so that unreacted hydrazine passes into the waste water as the semicarbazide is worked up. A number of hydrazines, especially phenyl hydrazines are, however, blood toxins for warmblooded animals, highly toxic to fish and because of their bactericidal properties are difficult to degrade biologically. The removal of phenyl hydrazines from waste water is therefore difficult to achieve.

According to a variant of the invention process therefore the manufacture of semicarbazides according to known processes may be combined with their further reaction to the triazoles of formula I by reacting hydrazine (a) with at least an equimolar quantity, preferably a low excess of up to 15 mol% of a cyanate (NaOCN, KOCN, NH$_4$OCN) in the pressure of about an equimole quantity of an organic or inorganic acid at 0° to 60° C. or (b) with at least the equimolar quantity, preferably an excess of up to 40 mol%, of urea in the presence of about 0.001 to 1.35 mols, preferably 0.1 to 1.35 mole (referred to the starting hydrazine) of an organic or inorganic acid or an ammonium salt thereof at 100° to 160° C., preferably 105° to 140° C., in one of the previously mentioned solvents, optionally under pressure, to give the semicarbazide II and subjecting the reaction mixture, after addition of formic acid and of further quantities of inorganic acid, to the reaction described to yield the compound I.

The total yield is improved and the waste water pollution is reduced by combining both process steps.

According to the invention process, the hydroxytriazoles of the formula I are obtained in excellent yield and in a high purity, which renders a subsequent purification superfluous for most uses, for example for the production of pesticides. If the process is performed in aqueous or aqueous-organic solutions, technical formic acid (of about 85% concentration) can be used, which is an additional advantage of the invention process.

The following examples illustrate the invention:

EXAMPLE 1

1-Phenyl-3-hydroxy-1,2,4-triazole 151 g of 1-phenyl semicarbazide, 135.3 g (2.5 mols) of 85% formic acid (technical) and 25 g (0.25 mol) of concentrated sulfuric acid were stirred for six hours at 95° to 100° C. The viscous mass obtained was diluted with 400 ml of water and cooled. The precipitate consisting of 1-phenyl-1,2,4-triazolone-3 was filtered off and washed neutral with water. Drying at 100° C. and 200 mbar gave 145.5 g=90.3% of the theory, of 1-phenyl-1,2,4-triazolone-3 having a melting point of 285° to 286° C.

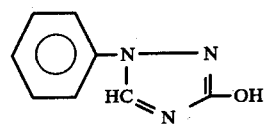

EXAMPLES 2 TO 17

The process was repeated under varied conditions (formic acid concentrations, reaction times, quantities of batches) using technical grade phenyl semicarbazide as starting compound. The results are shown in Table 1.

TABLE 1

Examples 2–17
1-Phenyl-2-hydroxy-1,2,4-triazole

| Example No. | Batch PSC[mol] | HCOOH[mol] | H$_2$O[ml] | H$_2$SO$_4$[mol] | Formic acid content of the aqueous solution | Reaction time [h] | Reaction temp. [°C.] | yield [% of the theory] | Mp. [°C.] |
|---|---|---|---|---|---|---|---|---|---|
| 2 | 1.0 | 2.0 | — | 0.25 | 100% | 3 | 110 | 86.5 | 286–7 |
| 3 | 1.0 | 2.5 | 20 | 0.25 | 85% | 4 | 110 | 89.5 | 285–6 |
| 4 | 1.0 | 2.5 | 20 | 0.10 | 85% | 24 | 110 | 90.6 | 289–91 |
| 5 | 1.0 | 2.5 | 20 | 0.15 | 85% | 6 | 110 | 90.3 | 287–9 |
| 6 | 1.0 | 3.0 | — | 0.25 | 100% | 6 | 110 | 87.4 | 284–5 |
| 7 | 1.0 | 2.5 | 45 | 0.25 | 71.9% | 6 | 105 | 90.3 | 285–7 |
| 8 | 1.0 | 2.5 | 85 | 0.25 | 57.5% | 16 | 105 | 92.0 | 285–6 |
| 9 | 1.0 | 2.5 | 85 | 0.25 | 57.5% | 4 | 105 | 91.0 | 283–4 |
| 10 | 1.0 | 2.5 | 320 | 0.25 | 26.4% | 16 | 100 | 91.8 | 285–6 |
| 11 | 1.0 | 2.5 | 320 | 0.25 | 26.4% | 4 | 100 | 90.0 | 285–6 |
| 12 | 1.0 | 2.5 | 520 | 0.25 | 18.1% | 16 | 100 | 89.7 | 285–6 |
| 13 | 1.0 | 2.5 | 270 | 0.25 | 40.3% | 4 | 95–100 | 89.8 | 283 |
| 14 (Comp.) | 1.0 | 2.5 | 20 | — | 85% | 6 | 95–100 | 8.7 | 282–4 |
| 15 | 1.0 | 2.0 | 270 | 0.25 | 40.3% | 4 | 95–100 | 87.6 | 285–6 |
| 16 | 1.0 | 1.3 | 270 | 0.25 | 40.3% | 24 | 95–100 | 86.5 | 280–2 |
| 17 | 1.0 | 1.5 | 270 | 0.25 | 40.3% | 16 | 95–100 | 88.6 | 280–2 |

Explanations referring to Table 1:
PSC = phenyl semicarbazide; yield, referred to technical PSC; H$_2$O: including the quantity of water contained in technical formic acid.

EXAMPLE 18

450.75 g (2.018 mols) of moist technical 1-phenyl-semicarbazide (solids content 67.6%), 300 ml of water, 270.6 g (5 mols) of technical 85% formic acid and 50 g (0.5 mol) of concentrated sulfuric acid were stirred for four hours at 95° C. The reaction solution was separated by filtration in vacuo and the mother liquor obtained, which, in addition to unreacted 1-phenyl semicarbazide, mainly contained formic acid and sulfuric acid was separated to be used in a further batch. The filter cake consisting of 1-phenyl-3-hydroxytriazole was subsequently washed neutral with water and dried in a vacuum drier. There were obtained 292.3 g (89.95% of the theory) of 1-phenyl-3-hydroxy-triazole having a melting point of 284°–285° C.

EXAMPLE 19

151 g of 1-phenyl semicarbazide, 108.25 g (2.0 mols) of technical 85% formic acid, 65 ml of water and 25 g (0.25 mol) of sulfuric acid were stirred for eight hours at 100° C. The batch was allowed to cool, 41.6 g (1.3 mols) of methanol were added dropwise, with methyl formate being separated by distillation through a column. The reaction mixture was left to stand at about 50° to 60° C., until completion of the methyl formate formation. Thereafter 400 ml of water were added, the mother liquor was filtered off, the filter cake was washed neutral with water and dried in vacuo. There were obtained 146.2 g (90.8% of the theory) of 1-phenyl-3-hydroxytriazole having a melting point of 286°-287° C.

EXAMPLE 20

185.5 g (1.0 mol) of 1-(4-chlorophenyl)-semicarbazide, 135.2 g (2.5 mols) of 85% formic acid, 40 ml of water and 30 g (0.3 mol) of concentrated sulfuric acid were heated for 6 hours at 95° C. Subsequently, 400 ml of water were added, the reaction mixture was separated by filtration, the filter cake was washed neutral with water and dried in a vacuum drying cabinet. There were obtained 170 g (87% of the theory) of 1-(4-chlorophenyl)-3-hydroxytriazole having a melting point of 305° C.

TABLE 2

Examples 21-32
The following compounds of the formula I were prepared analogously to Example 20:

| Example No. | R | yield [% of the theory] | Mp. [°C.] |
|---|---|---|---|
| 21 | F—⟨O⟩— | 88.6 | 298-300 |
| 22 | ⟨O⟩— (Cl) | 91.2 | 306 |
| 23 | Br—⟨O⟩— | 89.4 | 222-25 |
| 24 | ⟨O⟩— (NO₂) | 86.2 | 293-295 |
| 25 | NO₂—⟨O⟩— (CH₃) | 87.8 | 324 |
| 26 | NO₂—⟨O⟩— (NO₂) | 85.9 | 162-164 |
| 27 | ⟨O⟩— (CH₃) | 89.1 | 169-170 |
| 28 | ⟨O⟩— (CH₃) | 88.7 | 238-240 |
| 29 | CH₃—⟨O⟩— | 89.9 | 297 |
| 30 | ⟨O⟩— (C₂H₅) | 90.2 | 190-192 |
| 31 | C₂H₅OCO—⟨O⟩— | 86.1 | 160 |

TABLE 2-continued

Examples 21-32
The following compounds of the formula I were prepared analogously to Example 20:

| Example No. | R | yield [% of the theory] | Mp. [°C.] |
|---|---|---|---|
| 32 | Cl—⟨O⟩— (Cl) | 90.3 | 303-305 |

EXAMPLE 33

36.5 g of concentrated (30%) hydrochloric acid (0.3 mol) were added carefully to a solution of 151 g (1 mol) of 1-phenyl semicarbazide in 135.2 g (2.5 mols) of 85% formic acid and of 65 ml of water and the mixture was heated for 4 hours at 95° C. The mixture was diluted with 200 ml of water and filtered off. The filter cake was washed neutral with water and dried. There were obtained 142 g (88.2% of the theory) of 1-phenyl-3-hydroxytriazole having a melting point of 282°-283° C.

EXAMPLE 34 (single-pot process)

1-phenyl-3-hydroxy-1,2,4-triazole 225 g (2 mols) of technical 96% phenyl hydrazine, 221.2 g (2 mols) of 33% hydrochloride acid, 120 g (2 mols) of urea and 800 ml of water were heated for 5 hours at 125°-128° C. in a closed vessel in which a pressure of 2.6-2.8 atmospheres built up.

The reaction mixture was cooled to 100° C., whereupon 324.7 g (6 mols) of 85% formic acid and 50 g (0.5 mol) of concentrated sulfuric acid were added dropwise. The reaction mixture was stirred for a further 6 hours at 95° C. and cooled and the precipitated 1-phenyl-3-hydroxy-1,2,4-triazole was suction-filtered. (Excess formic acid can be recovered from the mother liquor by adding 144 g (4.5 mols) of methanol and distilling off the methyl formate formed (boiling point 32° C.)).

The filter cake was washed with water and dried in vacuo at 100° C., which gave 238.3 g (74% of the theory) of 1-phenyl-3-hydroxytriazole having a melting point of 280°-282° C.

EXAMPLE 35 (Single-pot process)

1-Phenyl-3-hydroxy-1,2,4-triazole 108 g (1 mol) of phenyl hydrazine and 60 g (1 mol) of urea were suspended in 500 ml of xylene and 111 g (1 mol) of concentrated sulfuric acid were added while stirring vigorously. The mixture was heated for 2.5 hours at 135° C. and water formed was separated via a water separator. After cooling to 90° C. 135.2 g (2.5 mols) of 85% formic acid and 25 g (0.25 mol) of concentrated sulfuric acid were added successively and the mixture was further heated for 6 hours at 95° C. After cooling, the product was filtered off, washed thoroughly with water until free from acid and dried in vacuo at 100° C. There were obtained 124.6 g (77.5% of the theory) of 1-phenyl-3-hydroxy-1,2,4-triazole having a melting point of 281°-282° C.

EXAMPLE 36 (Single-pot process)

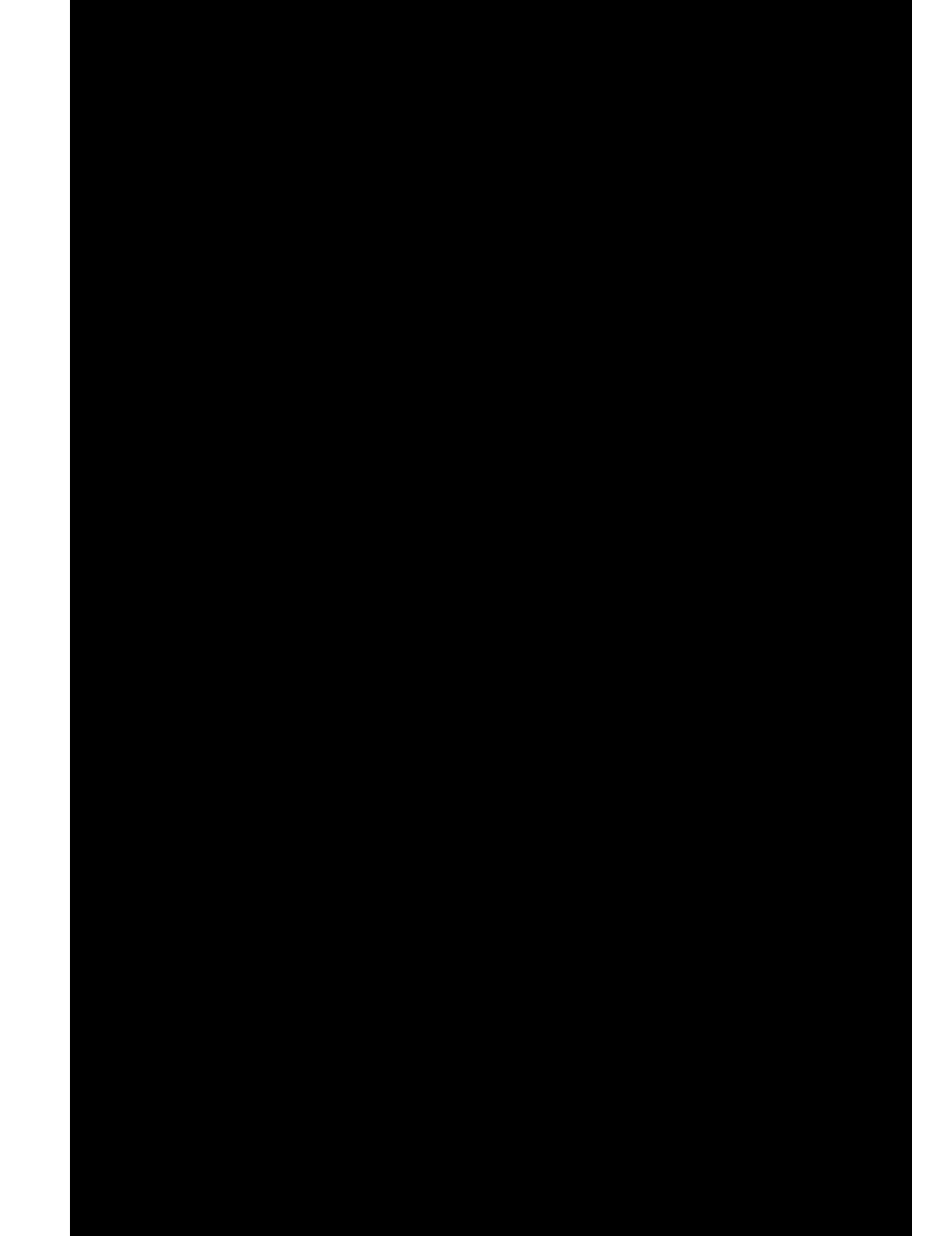

1-Phenyl-3-hydroxy-1,2,4-triazole 108 g (1 mol) of phenyl hydrazine, 60 g (1 mol) of urea and 300 ml of xylene were introduced into an